United States Patent [19]
Tessier-Lavigne et al.

[11] Patent Number: 6,017,714
[45] Date of Patent: Jan. 25, 2000

[54] NETRINS

[75] Inventors: Marc Tessier-Lavigne, San Mateo; Tito Serafini; Timothy Kennedy, both of San Francisco, all of Calif.; Marysia Placzek, London, United Kingdom; Thomas Jessell; Jane Dodd, both of New York, N.Y.

[73] Assignees: The Regents of the University of California, Oakland, Calif.; Columbia University, New York, N.Y.

[21] Appl. No.: 08/482,677

[22] Filed: Jun. 7, 1995

Related U.S. Application Data

[63] Continuation-in-part of application No. 08/152,019, Nov. 12, 1993, Pat. No. 5,565,331.
[51] Int. Cl.[7] .................. G01N 33/53; G01N 33/567; G01N 33/531
[52] U.S. Cl. .................. 435/7.1; 435/7.21; 435/7.8; 436/503; 436/543
[58] Field of Search ............................ 536/23.1; 435/7.1, 435/7.8, 7.21; 436/503, 543

[56] References Cited

U.S. PATENT DOCUMENTS 5,565,331  10/1996  Tessler-Lavigne .

OTHER PUBLICATIONS

Serafini et al, Cell 78(3) pp 409–425 (1994).
Kennedy et al, Cell 78(3) pp 425–435 (1994).
De La Torre et al, Society for Neuroscience Abstracts vol. 20, 1994 p. 1297.
Serafini et al *Cell* (1994) 78 pp. 409–424.
Letwack et al Abtracts Society for Neuroscience (1995) vol. 21 part 2 p. 1022.

*Primary Examiner*—Anthony C. Caputa
*Assistant Examiner*—Mark Navarro
*Attorney, Agent, or Firm*—Richard Aron Osman

[57] ABSTRACT

Netrin proteins, nucleic acids which encode netrin proteins and hybridization reagents, probes and primers capable of hybridizing with netrin genes and methods for screening chemical libraries for lead compounds for pharmacological agents are provided.

26 Claims, No Drawings

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1839 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
ATGATCACAT CAGTATTGCG CTATGTGCTA GCGCTCTACT TTTGTATGGG CATAGCTCAT      60

GGAGCATACT TTTCACAGTT CTCCATGAGA GCCCCAGACC ATGATCCTTG CCATGATCAT     120

ACTGGTCGAC CAGTTCGATG TGTTCCCGAG TTCATAAATG CTGCTTTTGG AAAACCTGTT     180

ATTGCTAGTG ATACATGCGG AACAAACCGA CCAGACAAGT ATTGTACTGT GAAGGAGGGT     240

CCGGATGGAA TTATCCGTGA GCAATGTGAC ACTTGTGATG CTAGAAACCA TTTCCAATCC     300

CATCCAGCCT CTCTTCTAAC TGATCTCAAT TCGATTGGAA ACATGACATG CTGGGTTTCC     360

ACTCCAAGTT TGAGCCCACA AAACGTTTCA CTCACTTTGT CACTCGGAAA AAAGTTTGAG     420

CTCACTTACG TCTCAATGCA CTTCTGTTCC CGTCTCCCAG ATTCAATGGC ACTTTACAAG     480

TCTGCTGACT TTGGAAAGAC CTGGACCCCG TTTCAATTCT ACTCCTCCGA ATGTCGTCGT     540

ATATTTGGCA GAGATCCCGA CGTGTCGATA ACAAAGTCAA ACGAGCAAGA AGCCGTTTGT     600

ACTGCCTCTC ATATAATGGG TCCAGGAGGA AACCGTGTAG CGTTCCCTTT TCTAGAGAAC     660

AGACCTTCTG CACAAAACTT CGAAAACTCG CCGGTGCTTC AGGATTGGGT CACCGCAACT     720

GACATTAAAG TGGTGTTTTC AAGGCTTAGT CCAGATCAGG CTGAACTGTA TGGCTTGTCT     780

AACGATGTCA ATTCGTACGG AAACGAGACG GATGATGAAG TCAAACAACG TTACTTCTAC     840
```

```
TCAATGGGAG AACTGGCAGT TGGTGGTCGC TGCAAATGTA ATGGTCACGC CAGTAGATGC      900

ATCTTTGACA AAATGGGCCG GTACACTTGT GACTGCAAGC ATAACACTGC CGGAACTGAA      960

TGCGAAATGT GCAAACCATT CCATTACGAT CGTCCATGGG AAGAGCCAC CGCAAATTCT      1020

GCCAACTCAT GTGTCGCTTG CAACTGCAAC CAACACGCAA AGAGATGCCG ATTCGATGCT     1080

GAGCTCTTTA GACTAAGTGG CAACCGGTCA GGAGGAGTGT GCTTGAACTG TCGTCATAAC     1140

ACTGCTGGAA GAAATTGTCA TCTCTGCAAA CCAGGATTTG TCCGTGATAC TTCTCTGCCA     1200

ATGACACATC GGAAAGCTTG TAAAGCTTGT GGATGTCATC CAGTCGGATC ACTTGGAAAA     1260

AGCTGCAACC AATCATCGGG TCAGTGCGTC TGCAAGCCTG GAGTCACTGG AACAACCTGT     1320

AATCGTTGTG CCAAAGGATA CCAACAAAGC CGTTCTACAG TTACTCCGTG TATCGAAATT     1380

CCGACCAAAG CTGATTTCAT TGGATCATCA CATTCAGAAG AGCAAGATCA GTGTTCGAAG     1440

TGCAGAATTG TTCCGAAGAG ACTCAACCAG AAGAAGTTCT GCAAGCGGGA TCATGCTGTC     1500

CAGATGGTTG TGGTCAGCCG TGAGATGGTT GATGGATGGG CCAAGTACAA GATTGTGGTT     1560

GAATCAGTTT TCAAACGAGG CACCGAGAAC ATGCAACGTG GCGAAACATC ATTGTGGATT     1620

TCCCCTCAAG GTGTCATTTG CAAGTGCCCA AAGCTCCGCG TCGACGCCG TTATCTCCTC      1680

CTTGGTAAGA ATGATTCCGA TCACGAGCGC GATGGATTGA TGGTCAATCC ACAGACTGTA    1740

TTGGTGGAAT GGGAGGACGA TATTATGGAT AAGGTACTAC GCTTCTCGAA AAAGATAAA     1800

CTTGGACAAT GCCCAGAGAT TACGTCACAC AGATACTGA                            1839
```

(2) INFORMATION FOR SEQ ID NO:2:

(i) SEQUENCE CHARACTERISTICS:
        (A) LENGTH: 612 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Ile Thr Ser Val Leu Arg Tyr Val Leu Ala Leu Tyr Phe Cys Met
1               5                   10                  15

Gly Ile Ala His Gly Ala Tyr Phe Ser Gln Phe Ser Met Arg Ala Pro
            20                  25                  30

Asp His Asp Pro Cys His Asp His Thr Gly Arg Pro Val Arg Cys Val
        35                  40                  45

Pro Glu Phe Ile Asn Ala Ala Phe Gly Lys Pro Val Ile Ala Ser Asp
    50                  55                  60

Thr Cys Gly Thr Asn Arg Pro Asp Lys Tyr Cys Thr Val Lys Glu Gly
65                  70                  75                  80

Pro Asp Gly Ile Ile Arg Glu Gln Cys Asp Thr Cys Asp Ala Arg Asn
                85                  90                  95

His Phe Gln Ser His Pro Ala Ser Leu Leu Thr Asp Leu Asn Ser Ile
            100                 105                 110

Gly Asn Met Thr Cys Trp Val Ser Thr Pro Ser Leu Ser Pro Gln Asn
        115                 120                 125

Val Ser Leu Thr Leu Ser Leu Gly Lys Lys Phe Glu Leu Thr Tyr Val
    130                 135                 140

Ser Met His Phe Cys Ser Arg Leu Pro Asp Ser Met Ala Leu Tyr Lys
145                 150                 155                 160

Ser Ala Asp Phe Gly Lys Thr Trp Thr Pro Phe Gln Phe Tyr Ser Ser
                165                 170                 175
```

-continued

```
Glu Cys Arg Arg Ile Phe Gly Arg Asp Pro Asp Val Ser Ile Thr Lys
            180                 185                 190

Ser Asn Glu Gln Glu Ala Val Cys Thr Ala Ser His Ile Met Gly Pro
        195                 200                 205

Gly Gly Asn Arg Val Ala Phe Pro Phe Leu Glu Asn Arg Pro Ser Ala
    210                 215                 220

Gln Asn Phe Glu Asn Ser Pro Val Leu Gln Asp Trp Val Thr Ala Thr
225                 230                 235                 240

Asp Ile Lys Val Val Phe Ser Arg Leu Ser Pro Asp Gln Ala Glu Leu
            245                 250                 255

Tyr Gly Leu Ser Asn Asp Val Asn Ser Tyr Gly Asn Glu Thr Asp Asp
        260                 265                 270

Glu Val Lys Gln Arg Tyr Phe Tyr Ser Met Gly Glu Leu Ala Val Gly
    275                 280                 285

Gly Arg Cys Lys Cys Asn Gly His Ala Ser Arg Cys Ile Phe Asp Lys
290                 295                 300

Met Gly Arg Tyr Thr Cys Asp Cys Lys His Asn Thr Ala Gly Thr Glu
305                 310                 315                 320

Cys Glu Asn Cys Lys Pro Phe His Tyr Asp Arg Pro Trp Gly Arg Ala
            325                 330                 335

Thr Ala Asn Ser Ala Asn Ser Cys Val Ala Cys Asn Cys Asn Gln His
        340                 345                 350

Ala Lys Arg Cys Arg Phe Asp Ala Glu Leu Phe Arg Leu Ser Gly Asn
    355                 360                 365

Arg Ser Gly Gly Val Cys Leu Asn Cys Arg His Asn Thr Ala Gly Arg
    370                 375                 380

His Cys His Leu Cys Lys Pro Gly Phe Val Arg Asp Thr Ser Leu Pro
385                 390                 395                 400

Met Thr His Arg Lys Ala Cys Lys Ser Cys Gly Cys His Pro Val Gly
            405                 410                 415

Ser Leu Gly Lys Ser Cys Asn Gln Ser Ser Gly Gln Cys Val Cys Lys
        420                 425                 430

Pro Gly Val Thr Gly Thr Thr Cys Asn Arg Cys Ala Lys Gly Tyr Gln
    435                 440                 445

Gln Ser Arg Ser Thr Val Thr Pro Cys Ile Lys Ile Pro Thr Lys Ala
450                 455                 460

Asp Phe Ile Gly Ser Ser His Ser Glu Glu Gln Asp Gln Cys Ser Lys
465                 470                 475                 480

Cys Arg Ile Val Pro Lys Arg Leu Asn Gln Lys Lys Phe Cys Lys Arg
            485                 490                 495

Asp His Ala Val Gln Met Val Val Ser Arg Glu Met Val Asp Gly
        500                 505                 510

Trp Ala Lys Tyr Lys Ile Val Val Glu Ser Val Phe Lys Arg Gly Thr
    515                 520                 525

Glu Asn Met Gln Arg Gly Glu Thr Ser Leu Trp Ile Ser Pro Gln Gly
530                 535                 540

Val Ile Cys Lys Cys Pro Lys Leu Arg Val Gly Arg Arg Tyr Leu Leu
545                 550                 555                 560

Leu Gly Lys Asn Asp Ser Asp His Glu Arg Asp Gly Leu Met Val Asn
            565                 570                 575

Pro Gln Thr Val Leu Val Glu Trp Glu Asp Asp Ile Met Asp Lys Val
        580                 585                 590
```

```
Leu Arg Phe Ser Lys Lys Asp Lys Leu Gly Gln Cys Pro Glu Ile Thr
        595                 600                 605

Ser His Arg Tyr
    610

(2) INFORMATION FOR SEQ ID NO:3:

(i) SEQUENCE CHARACTERISTICS:
        (A) LENGTH: 1921 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

ATGCCGCGGA GGGGCGCGGA GGGGCCGCTC GCCCTGCTGC TGGCGGCCGC GTGGCTGGCA      60

CAGCCGCTGC GAGGCGGCTA CCCCCTGAAC ATGTTCGCCG TGCAGACGCA GCCGACCCCT     120

GCTACGACGA GCACGGGCTG CCCCCCGCTG CATCCCGGAC TTCGTCAACT CGGCCTTCGG     180

CAAGGAGGTG AAGGTGTCGA GCACCTGCGG GAAGCCGCCG TCGAGGTACT GCGTGGTGAC     240

GGAGAAGGGC GAGGAGCAGG TCCGCTCGTG CCACCTCTGC AACGCCTCCG ACCCCAAGCG     300

CGCCCACCCG CCCTCCTTCC TCACCGACCT CAACAACCCG CACAACCTGA CGTGCTGGCA     360

GTCCGACAGC TACGTGCAGT ACCCGCACAA CGTCACCCTC ACGCTGTCCC TCGGCAAGAA     420

GTTCGAGGTG ACCTACGTGA GCCTGCAGTT CTGCTCGCCG CGCCCCGAGT CCATGGCCAT     480

CTACAAGTCC ATGGACTACG GCAAGACGTG GGTGCCCTTC CAGTTCTACT CCACGCAGTG     540

CCGCAAGATG TACAACAAGC CGAGCCGCGC CGCCATCACC AAGCAGAACG AGCAGGAGGC     600

CATCTGCACC GACTCGCACA CCGACGTGCG GCCCCTCTCC GGCGGCCTCA TCGCCTTCAG     660

CACCCTGGAC GGCCGCCCCA CCGCCCACGA CTTCGACAAC TCGCCCGTGC TGCAGGACTG     720

GGTGACGGCC ACCGACATCA AGGTGACCTT CAGCCGCCTG CACACCTTCG GCGACGAGAA     780

CGAGGACGAC TCCGAGCTCG CCCGCGACTC CTACTTCTAC GCCGTGTCCG ACCTGCAGGT     840

CGGCGGGCGC TGCAAGTGCA ACGGGCACGC GTCCCGCTGC GTCCGCGACC GCGACGACAA     900

CCTGGTGTGC GACTGCAAGC ACAACACGGC CGGGCCCGAG TGCGACCGCT GCAAACCCTT     960

CCACTACGAC CGGCCCTGGC AGAGGGCGAC CGCCCGAGAG GCCAACGAGT GCGTGGCCTG    1020

CAACTGCAAC CTGCATGCAC GGCGCTGCCG CTTCAACATG GAGCTGTACA AGCTGTCGGG    1080

CAGAAAGAGC GGCGGTGTCT GCCTCAACTG CCGGCACAAC ACGGCCGGGC GGCACTGCCA    1140

CTACTGCAAG GAAGGCTTCT ACCGCGACCT CAGCAAACCC ATCTCCCACC GCAAGGCCTG    1200

CAAAGAGTGC GATTGCCATC CGTGGGCGC CGCCGGCCAA ACCTGCAACC AAACCACGGG    1260

GCAGTGTCCA TGCAAGGACG CGTCACCGG CATCACCTGC AACCGCTGCG CCAAGGGCTA    1320

CCAGCAGAGC CGCTCGCCCA TTGCCCCCTG CATAAAGATC CCCGCCGCGC CGCCCCCCAC    1380

AGCTGCCAGC AGCACGGAGG AGCCTGCAGA CTGTGACTCG TACTGCAAAG CCTCCAAGGG    1440

GAAGCTGAAG ATCAACATGA AGAAGTACTG CAAGAAGGAC TACGCTGTGC AGATCCACAT    1500

CCTGAAAGCG GAAAAAAATG CCGACTGGTG GAAGTTCACC GTCAACATCA TCTCTGTCTA    1560

CAAACAGGGC AGCAACCGGC TGCGGCGCGG GGACCAGACC CTGTGGGTGC ACGCCAAGGA    1620

CATCGCCTGC AAGTGCCCCA AGGTGAAGCC CATGAAGAAG TACCTCCTGC TGGGCAGCAC    1680

CGAGGACTCT CCCGACCAGA GCGGCATCAT CGCGGACAAG AGCAGCCTGG TGATCCAATG    1740

GCGGGACACG TGGGCACGGC GGCTGCGGAA GTTCCAGCAG AGGGAGAAGA AGGGGAAGTG    1800

TAGGAAGGCG TAGGGAGGAG CGGTGATGGA CTGAGCGCTG CCGGGTGCGG GCGGGGGGTG    1860
```

GGCGCAGGGG GCTCACGGCA TCTCGTATTG AGGGATGGAA GGGGAAAAAA AACACGAAAC     1920

C     1921

(2) INFORMATION FOR SEQ ID NO:4:

(i) SEQUENCE CHARACTERISTICS:
        (A) LENGTH: 605 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Pro Arg Arg Gly Ala Glu Gly Pro Leu Ala Leu Leu Ala Ala
 1               5                  10                  15

Ala Trp Leu Ala Gln Pro Leu Arg Gly Gly Tyr Pro Xaa Leu Asn Met
                 20                  25                  30

Phe Ala Val Gln Thr Xaa Ala Asp Pro Cys Tyr Asp Glu His Gly Leu
                 35                  40                  45

Pro Xaa Arg Cys Ile Pro Asp Phe Val Asn Ser Ala Phe Gly Lys Glu
     50                  55                  60

Val Lys Val Ser Ser Thr Cys Gly Lys Pro Pro Ser Arg Tyr Cys Val
 65                  70                  75                  80

Val Thr Glu Lys Gly Glu Glu Gln Val Arg Ser Cys His Leu Cys Asn
                 85                  90                  95

Ala Ser Asp Pro Lys Arg Ala His Pro Pro Ser Phe Leu Thr Asp Leu
                100                 105                 110

Asn Asn Pro His Asn Leu Thr Cys Trp Gln Ser Asp Ser Tyr Val Gln
                115                 120                 125

Tyr Pro His Asn Val Thr Leu Thr Leu Ser Leu Gly Lys Lys Phe Glu
                130                 135                 140

Val Thr Tyr Val Ser Leu Gln Phe Cys Ser Pro Arg Pro Glu Ser Met
145                 150                 155                 160

Ala Ile Tyr Lys Ser Met Asp Tyr Gly Lys Thr Trp Val Pro Phe Gln
                165                 170                 175

Phe Tyr Ser Thr Gln Cys Arg Lys Met Tyr Asn Lys Pro Ser Arg Ala
                180                 185                 190

Ala Ile Thr Lys Gln Asn Glu Gln Glu Ala Ile Cys Thr Asp Ser His
                195                 200                 205

Thr Asp Val Arg Pro Leu Ser Gly Gly Leu Ile Ala Phe Ser Thr Leu
                210                 215                 220

Asp Gly Arg Pro Thr Ala His Asp Phe Asp Asn Ser Pro Val Leu Gln
225                 230                 235                 240

Asp Trp Val Thr Ala Thr Asp Ile Lys Val Thr Phe Ser Arg Leu His
                245                 250                 255

Thr Phe Gly Asp Glu Asn Glu Asp Asp Ser Glu Leu Ala Arg Asp Ser
                260                 265                 270

Tyr Phe Tyr Ala Val Ser Asp Leu Gln Val Gly Gly Arg Cys Lys Cys
                275                 280                 285

Asn Gly His Ala Ser Arg Cys Val Arg Asp Arg Asp Asp Asn Leu Val
                290                 295                 300

Cys Asp Cys Lys His Asn Thr Ala Gly Pro Glu Cys Asp Arg Cys Lys
305                 310                 315                 320

Pro Phe His Tyr Asp Arg Pro Trp Gln Arg Ala Thr Ala Arg Glu Ala
                325                 330                 335
```

```
Asn Glu Cys Val Ala Cys Asn Cys Asn Leu His Ala Arg Arg Cys Arg
            340                 345                 350

Phe Asn Met Glu Leu Tyr Lys Leu Ser Gly Arg Lys Ser Gly Gly Val
            355                 360                 365

Cys Leu Asn Cys Arg His Asn Thr Ala Gly Arg His Cys His Tyr Cys
            370                 375                 380

Lys Glu Gly Phe Tyr Arg Asp Leu Ser Lys Pro Ile Ser His Arg Lys
385                 390                 395                 400

Ala Cys Lys Glu Cys Asp Cys His Pro Val Gly Ala Ala Gly Gln Thr
                405                 410                 415

Cys Asn Gln Thr Thr Gly Gln Cys Pro Cys Lys Asp Gly Val Thr Gly
            420                 425                 430

Ile Thr Cys Asn Arg Cys Ala Lys Gly Tyr Gln Gln Ser Arg Ser Pro
            435                 440                 445

Ile Ala Pro Cys Ile Lys Ile Pro Ala Ala Pro Pro Thr Ala Ala
            450                 455                 460

Ser Ser Thr Glu Glu Pro Ala Asp Cys Asp Ser Tyr Cys Lys Ala Ser
465                 470                 475                 480

Lys Gly Lys Leu Lys Ile Asn Met Lys Lys Tyr Cys Lys Lys Asp Tyr
                485                 490                 495

Ala Val Gln Ile His Ile Leu Lys Ala Glu Lys Asn Ala Asp Trp Trp
                500                 505                 510

Lys Phe Thr Val Asn Ile Ile Ser Val Tyr Lys Gln Gly Ser Asn Arg
            515                 520                 525

Leu Arg Arg Gly Asp Gln Thr Leu Trp Val His Ala Lys Asp Ile Ala
530                 535                 540

Cys Lys Cys Pro Lys Val Lys Pro Met Lys Lys Tyr Leu Leu Leu Gly
545                 550                 555                 560

Ser Thr Glu Asp Ser Pro Asp Gln Ser Gly Ile Ile Ala Asp Lys Ser
                565                 570                 575

Ser Leu Val Ile Gln Trp Arg Asp Thr Trp Ala Arg Arg Leu Arg Lys
            580                 585                 590

Phe Gln Gln Arg Glu Lys Lys Gly Lys Cys Arg Lys Ala
            595                 600                 605

(2) INFORMATION FOR SEQ ID NO:5:

(i) SEQUENCE CHARACTERISTICS:
        (A) LENGTH: 2779 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

TCCTGCGCCT GCTGCTCACC ACCAGCGTGC TCCGCCTGGC ACGAGCTGCA AACCCCTTCG      60

TGGCTCAGCA GACTCCCCCA GACCCCTGCT ACGATGAGAG CGGGGCTCCC CCGCGCTGCA     120

TCCCCGAGTT CGTCAACGCC GCCTTTGGGA AGGAGGTGCA GGCTTCCAGC ACCTGTGGGA     180

AGCCCCCAAC ACGGCACTGC GATGCCTCGG ACCCCCGCCG AGCCCACCCA CCCGCCTACC     240

TGACCGACCT CAACACCGCC GCCAACATGA CGTGCTGGCG CTCCGAGACC CTGCACCACC     300

TGCCCCACAA CGTCACCCTC ACCCTTTCCC TCGGCAAGAA GTTTGAGGTG GTCTACGTCA     360

GCCTCCAGTT CTGCTCGCCC CGGCCGGAGT CCACCGCCAT CTTCAAGTCC ATGGACTACG     420

GCAAGACGTG GGTCCCCTAC CAGTACTACT CCTCGCAGTG CCGCAAGATC TACGGCAAGC     480
```

-continued

```
CCAGCAAGGC CACCGTCACC AAGCAGAACG AGCAGGAGGC GCTGTGCACC GATGGCCTCA      540

CCGACCTCTA CCCGCTCACT GGCGGCCTCA TCGCCTTCAG CACGCTCGAC GGGCGGCCCT      600

CGGCCCAGGA CTTCGACAGC AGCCCTGTGC TGCAGGACTG GGTGACGGCC ACCGACATCC      660

GGGTGGTGTT CAGCCGTCCC CACCTCTTCC GCGAGCTGGG GGGCCGCGAG GCTGGCGAGG      720

AGGACGGGGG GGCCGGGGCC ACCCCCTACT ACTACTCGGT GGGCGAGCTG CAGGTCGGCG      780

GGCGCTGCAA GTGCAACGGG CACGCCTCGC GCTGCGTCAA GGACAAGGAG CAGAAGCTGG      840

TGTGTGACTG CAAGCACAAC ACCGAGGGGC CCGAGTGCGA CCGCTGCAAG CCCTTCCACT      900

ACGACCGGCC GTGGCAGCGG GCCAGCGCCC GCGAGGCCAA CGAGTGCCTG GCCTGCAACT      960

GCAACCTGCA CGCTCGGCGC TGCCGCTTCA ACATGGAGCT GTATAAGCTG TCCGGCAGGA     1020

AGAGCGGCGG CGTTTGCCTC AACTGCCGAC ACAACACGGC TGGGAGGCAC TGCCACTACT     1080

GCAAGGAGGG CTTCTACCGG GACCTCAGCA AGTCCATCAC GGACCGCAAG GCCTGCAAAG     1140

CCTGTGACTG CCACCCAGTT GGTGCTGCTG GCAAGACCTG CAACCAAACA ACAGGGCAGT     1200

GCCCGTGCAA GGACGGCGTG ACCGGCCTCA CCTGCAACCG CTGCGCCAAG GCTTCCAGC      1260

AGAGCCGCTC GCCTGTGGCC CCCTGCATCA AGATCCCTGC CATCAACCCG ACCTCTCTTG     1320

TCACCAGCAC GGAGGCACCT GCAGACTGTG ACTCCTACTG CAAGCCAGCC AAAGGCAACT     1380

ACAAGATTAA CATGAAGAAG TACTGCAAGA AGGATTACGT GGTCCAAGTG AACATTTTGG     1440

AAATGGAGAC GGTGGCCAAC TGGGCCAAGT TCACCATCAA CATCCTCTCT GTCTACAAGT     1500

GCCGCGACGA GCGGGTCAAG CGCGGAGACA ACTTCTTGTG GATCCACCTC AAGGACCTGT     1560

CCTGCAAGTG CCCCAAAATC CAGATCAGCA AGAAGTACCT GGTGATGGGC ATCAGCGAGA     1620

ACTCCACCGA CCGGCCGGGA CTGATGGCCG ACAAGAACAG CCTGGTCATC CAGTGGAGGG     1680

ACGCCTGGAC TCGCCGCCTT CGGAAACTGC AGCGGAGGGA GAAGAAGGG AAGTGTGTGA      1740

AGCCCTGAGG GCCTCGTGCC CCACGCGGGT CCCGGCCCCA CTGCACACGC AGACCATGCC     1800

CAGAGACTCT GTACATACAT ATCGTGTGAA CGGACTCTTC TGTCTATAGT GTATATTTTG     1860

GCAACGGTTC CCCTTTTTGT GTGCGTGTGC ACGCGTGGGT GTGTGCACGT GTGTGTGCGT     1920

GTGTGTGTGT GTGTGTGTGT GTGTCTCCTC TCAGTGTGTA TTAAAAATAA GGCGGTAATG     1980

ACAAACCTTT AATGAGGAGC AAAGCAGAGG GGGTCCTGTG GGTGCCTGCT GCCTGAAGGA     2040

GCTTGAGGGG CTGGTTTCTT GCTCCGGGCG TGCTGTTCCT CACCCTTCTG TCCTACTCTC     2100

TCTTTCCCCT TGAGCAAAAC CTTCTGCCCA GTGCTGCTGT CTGAGCTCGC GGCTCTCCCT     2160

GCTGCAGAGC CCGGTCCCTC TCACGTGCTG CACATGTGCT GCTCTCAGCT CTCTGTGCCC     2220

CTTTTCTTGT GCAGCAGAGA CGGGAGGTCG GTTTCCTCCA TCCCGCTGCA CACACGGACC     2280

GGCTGGGTGG AGACCATCCA GCGCTGCAGG ACCGGCCCCA GGAGCTCCGC TGGGAGAACC     2340

AAGTGACCTT TCTCCAGGCC TGATCCTGCA GGACCTCAGC TTTACATGGA CTGGTCGTGC     2400

CGCCCAGGGG CAGGGCCCAT GGAAGTCTTG GGACAGCCA GGGCTGTTGG CCACCACCCC      2460

ACAGAGCTGT TCTGAGCAGG GCGCAGGGGT CTGCCTGTCC TGGTGCGTGG TCCAGGTGAC     2520

CCACAGGAAA GACCTGCAGA TACCCATATT CTCCTCTCGT GCCAGCTCTG CATGCTGCTG     2580

TGACCTTGGC CGTGCCAGAG GTGCAGAGGC AGAGGTGGCA GGAAGAGAGG AGAGCTTTCG     2640

CTGACCAACC TCCAGTCTTT CATTTCTTCT CATACTGTAT TAGTCTCCAG TTCAAACAGA     2700

CATCAGTTTC TTTCCACGTT GAGGTTATAG TGGTCTCGAG TAATAAACAT GAATGGAAAT     2760

AATAAAAAAA AAAAAAAA                                                   2779
```

(2) INFORMATION FOR SEQ ID NO:6:

(i) SEQUENCE CHARACTERISTICS:
        (A) LENGTH: 581 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu Arg Leu Leu Leu Thr Thr Ser Val Leu Arg Leu Ala Arg Ala Ala
1               5                   10                  15

Asn Pro Phe Val Ala Gln Gln Thr Pro Pro Asp Pro Cys Tyr Asp Glu
            20                  25                  30

Ser Gly Ala Pro Pro Arg Cys Ile Pro Glu Phe Val Asn Ala Ala Phe
        35                  40                  45

Gly Lys Glu Val Gln Ala Ser Ser Thr Cys Gly Lys Pro Pro Thr Arg
    50                  55                  60

His Cys Asp Ala Ser Asp Pro Arg Arg Ala His Pro Pro Ala Tyr Leu
65                  70                  75                  80

Thr Asp Leu Asn Thr Ala Ala Asn Met Thr Cys Trp Arg Ser Glu Thr
                85                  90                  95

Leu His His Leu Pro His Asn Val Thr Leu Thr Leu Ser Leu Gly Lys
            100                 105                 110

Lys Phe Glu Val Val Tyr Val Ser Leu Gln Phe Cys Ser Pro Arg Pro
        115                 120                 125

Glu Ser Thr Ala Ile Phe Lys Ser Met Asp Tyr Gly Lys Thr Trp Val
    130                 135                 140

Pro Tyr Gln Tyr Tyr Ser Ser Gln Cys Arg Lys Ile Tyr Gly Lys Pro
145                 150                 155                 160

Ser Lys Ala Thr Val Thr Lys Gln Asn Glu Gln Glu Ala Leu Cys Thr
                165                 170                 175

Asp Gly Leu Thr Asp Leu Tyr Pro Leu Thr Gly Gly Leu Ile Ala Phe
            180                 185                 190

Ser Thr Leu Asp Gly Arg Pro Ser Ala Gln Asp Phe Asp Ser Ser Pro
        195                 200                 205

Val Leu Gln Asp Trp Val Thr Ala Thr Asp Ile Arg Val Val Phe Ser
    210                 215                 220

Arg Pro His Leu Phe Arg Glu Leu Gly Gly Arg Glu Ala Gly Glu Glu
225                 230                 235                 240

Asp Gly Gly Ala Gly Ala Thr Pro Tyr Tyr Tyr Ser Val Gly Glu Leu
                245                 250                 255

Gln Val Gly Gly Arg Cys Lys Cys Asn Gly His Ala Ser Arg Cys Val
            260                 265                 270

Lys Asp Lys Glu Gln Lys Leu Val Cys Asp Cys Lys His Asn Thr Glu
        275                 280                 285

Gly Pro Glu Cys Asp Arg Cys Lys Pro Phe His Tyr Asp Arg Pro Trp
    290                 295                 300

Gln Arg Ala Ser Ala Arg Glu Ala Asn Glu Cys Leu Ala Cys Asn Cys
305                 310                 315                 320

Asn Leu His Ala Arg Arg Cys Arg Phe Asn Met Glu Leu Tyr Lys Leu
                325                 330                 335

Ser Gly Arg Lys Ser Gly Gly Val Cys Leu Asn Cys Arg His Asn Thr
            340                 345                 350

Ala Gly Arg His Cys His Tyr Cys Lys Glu Gly Phe Tyr Arg Asp Leu
        355                 360                 365
```

```
Ser Lys Ser Ile Thr Asp Arg Lys Ala Cys Lys Ala Cys Asp Cys His
    370                 375                 380

Pro Val Gly Ala Ala Gly Lys Thr Cys Asn Gln Thr Thr Gly Gln Cys
385                 390                 395                 400

Pro Cys Lys Asp Gly Val Thr Gly Leu Thr Cys Asn Arg Cys Ala Lys
                405                 410                 415

Gly Phe Gln Gln Ser Arg Ser Pro Val Ala Pro Cys Ile Lys Ile Pro
            420                 425                 430

Ala Ile Asn Pro Thr Ser Leu Val Thr Ser Thr Glu Ala Pro Ala Asp
        435                 440                 445

Cys Asp Ser Tyr Cys Lys Pro Ala Lys Gly Asn Tyr Lys Ile Asn Met
    450                 455                 460

Lys Lys Tyr Cys Lys Lys Asp Tyr Val Val Gln Val Asn Ile Leu Glu
465                 470                 475                 480

Met Glu Thr Val Ala Asn Trp Ala Lys Phe Thr Ile Asn Ile Leu Ser
                485                 490                 495

Val Tyr Lys Cys Arg Asp Glu Arg Val Lys Arg Gly Asp Asn Phe Leu
            500                 505                 510

Trp Ile His Leu Lys Asp Leu Ser Cys Lys Cys Pro Lys Ile Gln Ile
        515                 520                 525

Ser Lys Lys Tyr Leu Val Met Gly Ile Ser Glu Asn Ser Thr Asp Arg
    530                 535                 540

Pro Gly Leu Met Ala Asp Lys Asn Ser Leu Val Ile Gln Trp Arg Asp
545                 550                 555                 560

Ala Trp Thr Arg Arg Leu Arg Lys Leu Gln Arg Arg Glu Lys Lys Gly
                565                 570                 575

Lys Cys Val Lys Pro
            580

(2) INFORMATION FOR SEQ ID NO:7:

(i) SEQUENCE CHARACTERISTICS:
        (A) LENGTH: 1811 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

ATGATGCGCG CTGTGTGGGA GGCGCTGGCG GCGCTGGCGG CGGTGGCGTG CCTGGTGGGC      60

GCGGTCCGCG GGCCCGGGCT TAGCATGTTC GCCGGCCAGG CGGCGCAGCC TGATCCTTGC     120

TCGGATGAGA ATGGACACCC CGCCGCTGC ATCCCGGACT TTGTCAACGC CGCCTTCGGC      180

AAGGACGTGC GCGTGTCCAG CACCTGCGGC CGGCCCCCGG CGCGCTACTG CGTGGTGAGC     240

GAGCGTGGTG AAGAGCGCGT GCGCTCCTGT CACCTCTGCA ACTCTTCGGA TCCCAAGAAA     300

GCGCACCCGC CGCCTTCCT CACCGACCTC AATAACCCGC ACAACCTGAC GTGCTGGCAG      360

TCCGAGAACT ACCTGCAGTT CCCGCACAAC GTGACGCTCA CTCTGTCGCT CGGCAAGAAG     420

TTTGAGGTGA CCTATGTGAG CCTGCAATTC TGCTCGCCGC GGCCAGAGTC CATGGCCATC    480

TACAAGTCCA TGGACTACGG GCGCACGTGG GTGCCCTTCC AGTTCTATTC CACGCAGTGC    540

CGCAAAATGT ACAACCGGCC GCACCGCGCG CCTATCACCA AACAGAACGA GCAGGAGGCC    600

GTGTGCACCG ACTCGCACAC CGACATGCGC CCGCTCTCTG GCGGGCTGAT CGCTTTCAGC    660

ACGCTGGACG GGCGGCCCTC GGCGCACGAC TTCGACAACT CGCCGGTGCT GCAGGACTGG    720
```

-continued

```
GTCACGGCCA CCGACATCCG CGTGGCTTTC AGCCGCCTGC ACACGTTCGG CGACGAGAAC    780

GAAGACGACT CGGAGCTGGC GCGCGACTCC TATTACTATG CAGTGTCTGA CCTGCAGGTT    840

GGCGGCCGCT GCAAGTGCAA CGGCCACGCG GCGCGTTGCG TGCGCGACCG AGACGACAGT    900

CTGGTGTGTG ACTGTAGGCA CAACACGGCC GGCCCTGAAT GCGACCGTTG CAAGCCCTTC    960

CACTACGACC GGCCCTGGCA GCGCGCCACG GCCCGCGAGG CCAACGAGTG CGTGGCCTGC   1020

AACTGCAACC TCCATGCTCG GCGCTGCAGA TTCAACATGG AGCTCTATAA GCTATCAGGG   1080

CGCAAGAGCG GGGGAGTTGT CTCAACTGCC GCCACAACAC TGCGGGCCGC CACTGCCACT   1140

ACTGCAAGGA GGGCTTCTAC CGAGACATGG GCAAGCCTAT CACCCACCGG AAGGCTTGCA   1200

AAGCCTGTGA TTGCCACCCA GTGGGTGCTG CTGGCAAGAC CTGCAATCAA ACCACTGGCC   1260

AATGTCCCTG CAAGGACGGC GTGACGGGCA TCACCTGCAA CCGATGTGCC AAAGGCTACC   1320

AGCAGAGCCG TTCCCCCATC GCCCCTTGCA TCAAGATTCC TGTGGCGCCG CCCACCACTG   1380

CAGCCAGCAG CGTGGAGGAA CCGGAAGACT GTGATTCCTA TTGCAAGGCC TCCAAAGGCA   1440

AGCTGAAGAT GAACATGAAG AAATACTGCA GGAAGGACTA TGCTGTCCAG ATCCACATCC   1500

TGAAGGCCGA CAAAGCAGGG GACTGGTGGA AGTTCACCGT GAACATCATC TCCGTGTACA   1560

AGCAGGGCAC AAGTCGTATT CGCCGTGGTG ACCAGAGTTT GTGGATCCGC TCACGAGACA   1620

TCGCCTGCAA GTGTCCCAAA ATCAAGCCCC TCAAGAAGTA CTTGCTGTTG GGTAATGCCG   1680

AGGACTCACC TGACCAGAGT GGCATCGTGG CAGACAAGAG CAGCCTGGTG ATCCAGTGGC   1740

GGGACACATG GCACGGCGG CTGCGCAAGT TCCAGCAACG GGAGAAGAAG GGCAAGTGCA   1800

AGAAGGCCTA G                                                       1811
```

(2) INFORMATION FOR SEQ ID NO:8:

(i) SEQUENCE CHARACTERISTICS:
        (A) LENGTH: 603 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Met Arg Ala Val Trp Glu Ala Leu Ala Ala Leu Ala Ala Val Ala
 1               5                  10                  15

Cys Leu Val Gly Ala Val Arg Gly Pro Gly Leu Ser Met Phe Ala Gly
                20                  25                  30

Gln Ala Ala Gln Pro Asp Pro Cys Ser Asp Glu Asn Gly His Pro Arg
            35                  40                  45

Arg Cys Ile Pro Asp Phe Val Asn Ala Ala Phe Gly Lys Asp Val Arg
        50                  55                  60

Val Ser Ser Thr Cys Gly Arg Pro Pro Ala Arg Tyr Cys Val Val Ser
65                  70                  75                  80

Glu Arg Gly Glu Glu Arg Val Arg Ser Cys His Leu Cys Asn Ser Ser
                85                  90                  95

Asp Pro Lys Lys Ala His Pro Ala Phe Leu Thr Asp Leu Asn Asn
            100                 105                 110

Pro His Asn Leu Thr Cys Trp Gln Ser Glu Asn Tyr Leu Gln Phe Pro
        115                 120                 125

His Asn Val Thr Leu Thr Leu Ser Leu Gly Lys Lys Phe Glu Val Thr
    130                 135                 140

Tyr Val Ser Leu Gln Phe Cys Ser Pro Arg Pro Glu Ser Met Ala Ile
145                 150                 155                 160
```

-continued

```
Tyr Lys Ser Met Asp Tyr Gly Arg Thr Trp Val Pro Phe Gln Phe Tyr
            165                 170                 175

Ser Thr Gln Cys Arg Lys Met Tyr Asn Arg Pro His Arg Ala Pro Ile
            180                 185                 190

Thr Lys Gln Asn Glu Gln Glu Ala Val Cys Thr Asp Ser His Thr Asp
            195                 200                 205

Met Arg Pro Leu Ser Gly Gly Leu Ile Ala Phe Ser Thr Leu Asp Gly
            210                 215                 220

Arg Pro Ser Ala His Asp Phe Asp Asn Ser Pro Val Leu Gln Asp Trp
225                 230                 235                 240

Val Thr Ala Thr Asp Ile Arg Val Ala Phe Ser Arg Leu His Thr Phe
                245                 250                 255

Gly Asp Glu Asn Glu Asp Asp Ser Glu Leu Ala Arg Asp Ser Tyr Tyr
                260                 265                 270

Tyr Ala Val Ser Asp Leu Gln Val Gly Gly Arg Cys Lys Cys Asn Gly
                275                 280                 285

His Ala Ala Arg Cys Val Arg Asp Arg Asp Asp Ser Leu Val Cys Asp
            290                 295                 300

Cys Arg His Asn Thr Ala Gly Pro Glu Cys Asp Arg Cys Lys Pro Phe
305                 310                 315                 320

His Tyr Asp Arg Pro Trp Gln Arg Ala Thr Ala Arg Glu Ala Asn Glu
                325                 330                 335

Cys Val Ala Cys Asn Cys Asn Leu His Ala Arg Arg Cys Arg Phe Asn
                340                 345                 350

Met Glu Leu Tyr Lys Leu Ser Gly Arg Lys Ser Gly Gly Val Cys Leu
            355                 360                 365

Asn Cys Arg His Asn Thr Ala Gly Arg His Cys His Tyr Cys Lys Glu
370                 375                 380

Gly Phe Tyr Arg Asp Met Gly Lys Pro Ile Thr His Arg Lys Ala Cys
385                 390                 395                 400

Lys Ala Cys Asp Cys His Pro Val Gly Ala Ala Gly Lys Thr Cys Asn
                405                 410                 415

Gln Thr Thr Gly Gln Cys Pro Cys Lys Asp Gly Val Thr Gly Ile Thr
            420                 425                 430

Cys Asn Arg Cys Ala Lys Gly Tyr Gln Gln Ser Arg Ser Pro Ile Ala
            435                 440                 445

Pro Cys Ile Lys Ile Pro Val Ala Pro Pro Thr Thr Ala Ala Ser Ser
    450                 455                 460

Val Glu Glu Pro Glu Asp Cys Asp Ser Tyr Cys Lys Ala Ser Lys Gly
465                 470                 475                 480

Lys Leu Lys Met Asn Met Lys Tyr Cys Arg Lys Asp Tyr Ala Val
                485                 490                 495

Gln Ile His Ile Leu Lys Ala Asp Lys Ala Gly Asp Trp Trp Lys Phe
            500                 505                 510

Thr Val Asn Ile Ile Ser Val Tyr Lys Gln Gly Thr Ser Arg Ile Arg
            515                 520                 525

Arg Gly Asp Gln Ser Leu Trp Ile Arg Ser Arg Asp Ile Ala Cys Lys
            530                 535                 540

Cys Pro Lys Ile Lys Pro Leu Lys Lys Tyr Leu Leu Leu Gly Asn Ala
545                 550                 555                 560

Glu Asp Ser Pro Asp Gln Ser Gly Ile Val Ala Asp Lys Ser Ser Leu
                565                 570                 575
```

```
Val Ile Gln Trp Arg Asp Thr Trp Ala Arg Arg Leu Arg Lys Phe Gln
        580                 585                 590

Gln Arg Glu Lys Lys Gly Lys Cys Lys Lys Ala
        595                 600
```

(2) INFORMATION FOR SEQ ID NO:9:

(i) SEQUENCE CHARACTERISTICS:
        (A) LENGTH: 1743 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

```
ATGCCCACCT GGCTCTGGGG GCTGCTGCTG ACCGCGGGCA CGCTCTCCGC TGCACTGAGC      60
CCAGGGCTGC CGGCCTCTGC CGACCCCTGC TATGATGAAG CGAGGGAGCC TCGCTCTTGT     120
ATTCCTGGCC TTGTGAACGC TGCTCTGGGC CGAGAGGTGC TGGCGTCCAG CACGTGCGGG     180
AGGTCGGCCA ATCGCGTCTG CGATTCCTCG ACCCGCAGC GGGCTCACTC TGCAGACCTC      240
CTGACCTCTG CTCCGGGCAC TGCAAGTCCT CTCTGTTGGC GCTCCGATTT GCTGCAACAG     300
GCACCTTTCA ACGTAACCCT CACAGTGCCC TGGGGAAGG CTTTTGAGCT GGTCTTCGTG      360
AGCCTGCGCT TCTGCTCAGC TCCTCCAACC TCCGTGGCCC TGCTTAAGTC GCAGGACCAT     420
GGCCGCAGCT GGGTCCCCTT GGGCTTCTTC TCTTCCAGCT GTACCCTGGA CTATGGCCGT     480
CTGCCTGCTC CTGCTGATGG CCCTTCTGGT CCAGGGCCAG AAGCCCTCTG CTTTCCAGCC     540
CCCCAGGCTC AGCCTGATGG TGGAGGCCTT CTGGCCTTCA GTGTGCAGGA TGGCAGCCCA     600
CAGGGCCTGG ATCTGGACAA CAGCCCCGTG CTCCAAGACT GGGTGACTGC CACAGATATT     660
CGCATAGTAC TCACAAGGCC TGCCATTCAG GGAGACACCA GGGACGGTGG GGTGACAGTC     720
CCCTACTCCT ACTCAGCCAC TGAGCTTCAG GTGGGAGGTC GATGCAAGTG CAATGGGCAT     780
GCCTCACGGT GTCTGTTGGA CACCCATGGC CACCTGGTCT GCGACTGCCA GCATGGTACA     840
GAGGGCCCTG ATTGCAGCCG CTGCAAGCCC TTCTACTGCG ACAGGCCATG GCAGCGGGCT     900
ACAGGGCAGG AAGCCCACGC TTGCCTTGCT TGCTCCTGCA ACGGCCATGC GCGAAGATGC     960
CGCTTCAACA TGGAGCTCTA CCGACTGTCT GGCCGCCGCA GTGGGGGCGT GTGCTCCAAC    1020
TGCCGGCACA ATACAGCTGG TCGTCACTGC CACTACTGCC GGGAGGGCTT CTATCGTGAT    1080
CCAGGCCGTG TCCTGAGTGA CCGTCGTGCT TGCAGAGCTT GTGACTGCCA CCCAGTTGGT    1140
GCTGCTGGCA AAACCTGTAA CCAGACCACA GGCCAGTGTC CCTGTAAGGA TGGTGTTACT    1200
GGCCTCACCT GTAACCGCTG TGCCCCAGGT TTCCAGCAGA GCCGTTCTCC TGTGGCACCT    1260
TGCGTTAAGA CTCCTGTCCC TGGACCCACC GAAGAAAGCA GTCCTGTGGA GCCACAGGAC    1320
TGTGAGTCAC ATTGCAGACC TGCGCGTGGC AGTTACCGAA TCAGCCTGAA GAAGTTCTGC    1380
CGGAAGGACT ATGCGGTGCA GGTGGCAGTG GGTGCACGCG GTGAGGCCCG CGGCTCGTGG    1440
ACACGCTTTC CGGTAGCGGT GCTTGCTGTG TTCCGCAGCG GCGAGGAACG CGCTCGACGC    1500
GGGAGCAGCG CGCTGTGGGT ACCAACCCTA GACGCGGCCT GCGGTTGCCC GCGCCTCCTG    1560
CCTGGCCGGC GTTACTTGCT GCTGGGAGGT GGGCCGGGGG CTGCAGCTGG GAGCACAGCG    1620
GGCCGGGGAC AGGGGCTCAG TGCTGCCCGT GGAAGCCTCG TGCTGCCTTG GAGAGACGCC    1680
TGGACCCGGC GCCTGCGGAG GCTGCAGAGG AGAGAGCGGC GGGGGCGCTG CGGGACCGCC    1740
TGA                                                                 1743
```

-continued (2) INFORMATION FOR SEQ ID NO:10:

(i) SEQUENCE CHARACTERISTICS:
        (A) LENGTH: 580 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Pro Thr Trp Leu Trp Gly Leu Leu Leu Thr Ala Gly Thr Leu Ser
 1               5                  10                  15

Ala Ala Leu Ser Pro Gly Leu Pro Ala Ser Ala Asp Pro Cys Tyr Asp
            20                  25                  30

Glu Ala Arg Glu Pro Arg Ser Cys Ile Pro Gly Leu Val Asn Ala Ala
         35                  40                  45

Leu Gly Arg Glu Val Leu Ala Ser Ser Thr Cys Gly Arg Ser Ala Asn
 50                  55                  60

Arg Val Cys Asp Ser Ser Asp Pro Gln Arg Ala His Ser Ala Asp Leu
 65                  70                  75                  80

Leu Thr Ser Ala Pro Gly Thr Ala Ser Pro Leu Cys Trp Arg Ser Asp
                85                  90                  95

Leu Leu Gln Gln Ala Pro Phe Asn Val Thr Leu Thr Val Pro Leu Gly
               100                 105                 110

Lys Ala Phe Glu Leu Val Phe Val Ser Leu Arg Phe Cys Ser Ala Pro
           115                 120                 125

Pro Thr Ser Val Ala Leu Leu Lys Ser Gln Asp His Gly Arg Ser Trp
130                 135                 140

Val Pro Leu Gly Phe Phe Ser Ser Ser Cys Thr Leu Asp Tyr Gly Arg
145                 150                 155                 160

Leu Pro Ala Pro Ala Asp Gly Pro Ser Gly Pro Gly Pro Glu Ala Leu
                165                 170                 175

Cys Phe Pro Ala Pro Gln Ala Gln Pro Asp Gly Gly Gly Leu Leu Ala
            180                 185                 190

Phe Ser Val Gln Asp Gly Ser Pro Gln Gly Leu Asp Leu Asp Asn Ser
           195                 200                 205

Pro Val Leu Gln Asp Trp Val Thr Ala Thr Asp Ile Arg Ile Val Leu
210                 215                 220

Thr Arg Pro Ala Ile Gln Gly Asp Thr Arg Asp Gly Val Thr Val
225                 230                 235                 240

Pro Tyr Ser Tyr Ser Ala Thr Glu Leu Gln Val Gly Gly Arg Cys Lys
                245                 250                 255

Cys Asn Gly His Ala Ser Arg Cys Leu Leu Asp Thr His Gly His Leu
            260                 265                 270

Val Cys Asp Cys Gln His Gly Thr Glu Gly Pro Asp Cys Ser Arg Cys
           275                 280                 285

Lys Pro Phe Tyr Cys Asp Arg Pro Trp Gln Arg Ala Thr Gly Gln Glu
290                 295                 300

Ala His Ala Cys Leu Ala Cys Ser Cys Asn Gly His Ala Arg Arg Cys
305                 310                 315                 320

Arg Phe Asn Met Glu Leu Tyr Arg Leu Ser Gly Arg Ser Gly Gly
                325                 330                 335

Val Cys Ser Asn Cys Arg His Asn Thr Ala Gly Arg His Cys His Tyr
            340                 345                 350

Cys Arg Glu Gly Phe Tyr Arg Asp Pro Gly Arg Val Leu Ser Asp Arg
           355                 360                 365
```

```
Arg Ala Cys Arg Ala Cys Asp Cys His Pro Val Gly Ala Ala Gly Lys
            370                 375                 380

Thr Cys Asn Gln Thr Thr Gly Gln Cys Pro Cys Lys Asp Gly Val Thr
385                 390                 395                 400

Gly Leu Thr Cys Asn Arg Cys Ala Pro Gly Phe Gln Gln Ser Arg Ser
                405                 410                 415

Pro Val Ala Pro Cys Val Lys Thr Pro Val Pro Gly Pro Thr Glu Glu
            420                 425                 430

Ser Ser Pro Val Glu Pro Gln Asp Cys Glu Ser His Cys Arg Pro Ala
        435                 440                 445

Arg Gly Ser Tyr Arg Ile Ser Leu Lys Lys Phe Cys Arg Lys Asp Tyr
    450                 455                 460

Ala Val Gln Val Ala Val Gly Ala Arg Gly Glu Ala Arg Gly Ser Trp
465                 470                 475                 480

Thr Arg Phe Pro Val Ala Val Leu Ala Val Phe Arg Ser Gly Glu Glu
                485                 490                 495

Arg Ala Arg Arg Gly Ser Ser Ala Leu Trp Val Pro Thr Leu Asp Ala
            500                 505                 510

Ala Cys Gly Cys Pro Arg Leu Leu Pro Gly Arg Arg Tyr Leu Leu Leu
            515                 520                 525

Gly Gly Gly Pro Gly Ala Ala Ala Gly Ser Thr Ala Gly Arg Gly Gln
            530                 535                 540

Gly Leu Ser Ala Ala Arg Gly Ser Leu Val Leu Pro Trp Arg Asp Ala
545                 550                 555                 560

Trp Thr Arg Arg Leu Arg Arg Leu Gln Arg Arg Glu Arg Arg Gly Arg
                565                 570                 575

Cys Gly Thr Ala
            580

(2) INFORMATION FOR SEQ ID NO:11:

(i) SEQUENCE CHARACTERISTICS:
        (A) LENGTH: 727 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Met Ile Arg Gly Ile Leu Leu Leu Leu Gly Thr Thr Arg Phe Ser
1               5                   10                  15

Pro Ile Gln Cys Ile Phe Asn Asp Val Tyr Phe Lys Met Phe Ser Gln
            20                  25                  30

Gln Ala Pro Pro Glu Asp Pro Cys Tyr Asn Lys Ala His Glu Pro Arg
        35                  40                  45

Ala Cys Ile Pro Asp Phe Val Asn Ala Ala Tyr Asp Ala Pro Val Val
50                  55                  60

Ala Ser Ser Thr Cys Gly Ser Ser Gly Ala Gln Arg Tyr Cys Glu Tyr
65                  70                  75                  80

Gln Asp His Glu Arg Ser Cys His Thr Cys Asp Met Thr Asp Pro Leu
                85                  90                  95

Arg Ser Phe Pro Ala Arg Ser Leu Thr Asp Leu Asn Asn Ser Asn Asn
                100                 105                 110

Val Thr Cys Trp Arg Ser Glu Pro Val Thr Gly Ser Gly Asp Asn Val
            115                 120                 125
```

-continued

```
Thr Leu Thr Leu Ser Leu Gly Lys Lys Phe Glu Leu Thr Tyr Val Ile
    130                 135                 140
Leu Gln Leu Cys Pro His Ala Pro Arg Pro Asp Ser Met Val Ile Tyr
145                 150                 155                 160
Lys Ser Thr Asp His Gly Leu Ser Trp Gln Pro Phe Gln Phe Phe Ser
                165                 170                 175
Ser Gln Cys Arg Arg Leu Phe Gly Arg Pro Ala Arg Gln Ser Thr Gly
            180                 185                 190
Arg His Asn Glu His Glu Ala Arg Cys Ser Asp Val Thr Arg Pro Leu
        195                 200                 205
Val Ser Arg Ile Ala Phe Ser Thr Leu Glu Gly Arg Pro Ser Ser Arg
    210                 215                 220
Asp Leu Asp Ser Ser Pro Val Leu Gln Asp Trp Val Thr Ala Thr Asp
225                 230                 235                 240
Ile Arg Val Val Phe His Arg Leu Gln Arg Pro Asp Pro Gln Ala Leu
                245                 250                 255
Leu Ser Leu Glu Ala Gly Gly Ala Thr Asp Leu Ala Ser Gly Lys Tyr
            260                 265                 270
Ser Val Pro Leu Ala Asn Gly Pro Ala Gly Asn Asn Ile Glu Ala Asn
        275                 280                 285
Leu Gly Gly Asp Val Ala Thr Ser Gly Ser Gly Leu His Tyr Ala Ile
    290                 295                 300
Ser Asp Phe Ser Val Gly Gly Arg Cys Lys Cys Asn Gly His Ala Ser
305                 310                 315                 320
Lys Cys Ser Thr Asp Ala Ser Gly Gln Leu Asn Cys Glu Cys Ser His
                325                 330                 335
Asn Thr Ala Gly Arg Asp Cys Glu Arg Cys Lys Pro Phe His Phe Asp
            340                 345                 350
Arg Pro Trp Ala Arg Ala Thr Ala Lys Glu Ala Asn Glu Cys Lys Glu
        355                 360                 365
Cys Asn Cys Asn Lys His Ala Arg Gln Cys Arg Phe Asn Met Glu Ile
    370                 375                 380
Phe Arg Leu Ser Gln Gly Val Ser Gly Gly Val Cys Gln Asn Cys Arg
385                 390                 395                 400
His Ser Thr Thr Gly Arg Asn Cys His Gln Cys Lys Glu Gly Phe Tyr
                405                 410                 415
Arg Asp Ala Thr Lys Pro Leu Thr His Arg Lys Val Cys Lys Ala Cys
            420                 425                 430
Asp Cys His Pro Ile Gly Ser Ser Gly Lys Ile Cys Asn Ser Thr Ser
        435                 440                 445
Gly Gln Cys Pro Cys Lys Asp Gly Val Thr Gly Leu Thr Cys Asn Arg
    450                 455                 460
Cys Ala Arg Gly Tyr Gln Gln Ser Arg Ser His Ile Ala Pro Cys Ile
465                 470                 475                 480
Lys Gln Pro Pro Arg Met Ile Asn Met Leu Asp Thr Gln Asn Thr Ala
                485                 490                 495
Pro Glu Pro Asp Ala Pro Glu Ser Ser Pro Gly Ser Gly Gly Asp Arg
            500                 505                 510
Asn Gly Ala Ala Glu Trp Pro Pro Ser Leu Ser Thr Ile Ala Pro Arg
        515                 520                 525
Ala Ala Gly Val Lys Cys Gly Lys Cys Arg Val Ser Thr Lys Arg Leu
    530                 535                 540
Asn Leu Asn Lys Phe Cys Lys Arg Asp Tyr Ala Ile Met Ala Lys Val
545                 550                 555                 560
```

```
Ile Gly Arg Asp Thr Ser Ser Glu Ala Val Ser Arg Glu Val Gln Arg
            565                 570                 575

Arg Ala Met Asp Pro Asp Val Ala Asp Tyr Glu Met Asp Gln Val Gln
            580                 585                 590

Pro Gly Ser Ala Arg Ser Pro Ile Thr Gly Val Tyr Glu Phe Gln Ala
            595                 600                 605

Ala Asp Tyr Pro Asn Pro Asn Pro Asn Pro Arg Gly Ser Glu Met Glu
            610                 615                 620

Arg Phe Asp Leu Gln Ile Gln Ala Val Phe Lys Arg Thr Arg Pro Gly
625                 630                 635                 640

Glu Ser Ser Gly Ala Gly Asn Val Tyr Gly Met Pro Asn Thr Thr Leu
            645                 650                 655

Lys Arg Gly Pro Met Thr Trp Ile Ile Pro Thr Lys Asp Leu Glu Cys
            660                 665                 670

Arg Cys Pro Arg Ile Arg Val Asn Arg Ser Tyr Leu Ile Leu Gly Arg
            675                 680                 685

Asp Ser Glu Ala Pro Pro Gly Tyr Leu Gly Ile Gly Pro His Ser Ile
            690                 695                 700

Val Ile Glu Trp Lys Glu Asp Trp Tyr Arg Arg Met Lys Arg Phe Gln
705                 710                 715                 720

Arg Arg Ala Arg Thr Cys Ala
            725
```

(2) INFORMATION FOR SEQ ID NO:12:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GGCCCGGAGT GCGACCGCTG CAAGCCCTTC CACTACGACC GGCCCTGGCA GCGCGGCACA      60
GCCCGCGAAG CCAACGAGTG CGTGGGTGAG TGGGGTGCGG CGGCGGACGG                110
```

(2) INFORMATION FOR SEQ ID NO:13:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
CACACTTCGA CAACTCGCCC GTGCTGCAGG ACTGGGTCAC GGCCACAGAC ATCCGCGTGG      60
CCTTCAGCCG CCTGCACTCG TTCGGCGACG AGAACAGACA CTCGGA                   106
```

(2) INFORMATION FOR SEQ ID NO:14:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

| | | | | | |
|---|---|---|---|---|---|
|CTCGAGAAGC|TTCAGGACTA|GGTAACGGCG|ACCGACGTCC|GTGTAGTGCT|CACAAGGCCT 60|
|AGCACGGCAG|GTGACCCCAG|GGACATGGAG|GCCGTCGTCC|CTTACTCCTA|CGCAGCCACC 120|
|GACCTCCAGG|TGGGCGGGCG|CTGCAAGTGC|AATGGACATG|CCTCACGGTG|CCTGCTGGAC 180|
|ACACAGGGCC|ACCTGATCTG|CGACTGTCGG|CATGGCACCG|AGGGCCCTGA|CTGCGGCCGC 240|
|TGCAAACCTT|TTCACTTCGA|CGGATCCCTC|GAG| |273|

NETRINS

RELATED APPLICATION

This application is a continuation in part of Ser. No. 08/152,019 filed Nov. 12, 1993, issued as U.S. Pat. No. 5,565,311.

The research carried out in the subject application was supported in part by grants from the National Institutes of Health. The government may have rights in any patent issuing on this application.

INTRODUCTION

1. Field of the Invention

The field of this invention is vertebrate netrin proteins and genes which are involved in neural axon outgrowth.

2. Background

In the developing nervous system, axons project considerable distances along stereotyped pathways to reach their targets. Axon growth and guidance depends partly on the recognition of cell-surface and extracellular matrix cues along these pathways. The identification of such nerve cell growth and guidance cues is the holy grail of neurobiology. These are the compounds that tell neurons when to grow, where to grow, and when to stop growing. The medical applications of such compounds are enormous and include modulating neuronal growth regenerative capacity, treating neurodegenerative disease, and mapping (e.g. diagnosing) genetic neurological defects.

Over decades of concentrated research, various hypotheses involving chemo-attractants and repellents, labeled pathways, cell adhesion molecules, etc. have been invoked to explain guidance. Molecules such as N-CAM and N-cadherin have been reported to provide favorable substrates for axon growth and certain sensory axons may be responsive to NGF and NGF-like factors. Recent reports suggest the existence of diffusible chemotropic molecule(s) which influence the pattern and orientation of commissural axon growth.

Relevant Literature

Placzek et al. (1990) Development 110, 19–30; Placzek et al. (1990) Cold Spring Harbor Symposia on Quantitative Biology 55, 279–302.; and Tessier-Lavigne et al. (1988) Nature 336: 775–778 report evidence for diffusible chemotropic molecules which influence the pattern and orientation of commissural axon growth. Gundersen and Barret (1980) JCB 87, 546–554, Lohof et al. (1992) J. Neurosci. 12 (4), 1253–1261 and Zheng et al. (1993) Soc. Neurosci. Abstr 19, 608.9 report neural chemotaxis in response to NGF, cAMP and acetylcholine, respectively. Ishii et al. (1992) Neuron 9, 873–881 disclose a gene, unc-6, derived from *C. elegans*, which has sequence similarity to the disclosed netrins. Data disclosed in this application was published in Serafini et al (1994) Cell 78, 409–424 and Kennedy et al (1994) Cell 78, 425–435 at page 5, column 1. The work was also reported in *The New York Times*, Section B7, Tuesday, Aug. 16, 1994 and more recently (May 19, 1995) described in Science 268, 971–973 (see also references cited therein).

SUMMARY OF THE INVENTION

The invention provides methods and compositions relating to netrins and netrin genes. Netrins are a novel class of proteins which are naturally involved in neural axon guidance. The subject compositions include nucleic acids which encode netrin proteins and hybridization probes and primers capable of hybridizing with netrin genes. Netrins find particular use in modulating neural axon outgrowth. The disclosed compositions also find use variously in screening chemical libraries for regulators of axon outgrowth and orientation, in genetic mapping, as probes for related genes, as diagnostic reagents for genetic neurological disease and in the production of specific cellular and animal systems for the development of neurological disease therapy.

DETAILED DESCRIPTION OF THE INVENTION

The invention provides methods and compositions relating to netrins and netrin genes; including methods and compositions for identifying, purifying, characterizing, and producing netrins and for identifying, characterizing, cloning, expressing, inhibiting the expression of and amplifying netrin genes.

Netrins are characterized by sequence similarity to the disclosed netrins 1 and 2. Using the amino acid sequence search program BLASTP (Altschul et al. (1990) Basic Local Alignment Search Tool, J Mol Biol 215, 403–410), complete (full length) netrin amino acid sequences provide a Probability P(N) score of less than $1.0e^{-200}$. In contrast, complete amino acid sequence comparison of a netrin with the evolutionarily related laminin proteins provides P(N) scores exceeding $1.0e^{-144}$. In addition, netrins generally show at least about 25% overall pair-wise sequence identity with all of the disclosed netrins 1 and 2 and at least about 50% pair-wise sequence identity within domain V. Furthermore, netrins are generally characterized by netrin-specific amino acid sequences invariant across the disclosed netrins 1 and 2 as seen in their Amino Acid Alignments. The subject netrins may be incomplete translates of the disclosed netrin cDNA sequences or deletion mutants of the corresponding conceptual translates, which translates or deletion mutants have the netrin binding activity and specificity described herein. Netrin peptides of the invention comprise unique portions of the disclosed netrin polypeptides and netrin receptors. A "unique portion" has an amino acid sequence unique to that disclosed in that it is not found in any previously known protein and has a length at least long enough to define a novel peptide. Unique portions are found to vary from about 5 to about 25 residues, preferably from 5 to 10 residues in length, depending on the particular amino acid sequence and are readily identified by comparing the subject portion sequences with known peptide/protein sequence data bases. Preferred unique portions include netrin residues that directly bind and activate (agonize) netrin receptors, especially residues that derive from the EGF-like domains of the disclosed sequences, especially those of the human varieties.

Particular preferred netrin peptides are listed here. These peptides are shown by functional assays disclosed herein to have biological activity including axon outgrowth and/or orienting activity. It is apparent to those of ordinary skill in the art that substitutions of chemically conservative residues can be made while preserving function.

Preferred peptides derived from domain V of netrin 2 and netrin 1:

1. NGH AA/SR (SEQ ID NO:04/06, residues 289–294/ 265–270)
2. VRD RDD N/SLV (SEQ ID NO:04, residues 296–304)
3. VKD KEQ KLV (SEQ ID NO:06, residues 272–280)
4. KHN TE/AG PE (SEQ ID NO:04/06, residues 308–315/ 284–291)
5. KPF HYD DRP WQR AT/SA REA NE (SEQ ID NO:04/ 06, residues 320–338/296–319)

6. NLH ARR (SEQ ID NO:04, residues 345–350)
7. RFN MEL YKL SGR KSG GV (SEQ ID NO:04/06, residues 352–368/328–344)
8. RHN TAG RH (SEQ ID NO:04/06, residues 373–380/349–356)
9. KEG FYR DLS KP/SIS/TH/DR KA (SEQ ID NO:04/06, residues 385–401/361–377)
10. HPV GAA GK/QT (SEQ ID NO:04/06, residues 408–416/384–392)
11. NQT TGQ (SEQ ID NO:04/06, residues 418–423/394–399)
12. KDG VTG I/LT (SEQ ID NO:04/06, residues 427–434/403–410)
13. AKG Y/FQQ SRS PI/VA P (SEQ ID NO:04/06, residues 439–451/415–427)

Preferred peptides derived from the C terminal domains of netrin 2 and netrin 1:

14. IKI PAI/AN/P (SEQ ID NO:04/06, residues 454–460/429–435)
15. IKI PVR (SEQ ID NO:08, residues 451–456)
16. STE A/EPA DCD SYC K (SEQ ID NO:04/06, residues 466–478/442–454)
17. KI/MN MKK YCK/R KDY V/AVQ (SEQ ID NO:04/06, residues 485–499/461–475)
18. KFT I/VNI L/T/ISV YK (SEQ ID NO:04/06, residues 513–523/489–499)
19. CKC PKI/V (SEQ ID NO:04/06, residues 545–550/521–526)
20. ADK S/NSL VIQ WRD (SEQ ID NO:04/06, residues 573–584/549–560)
21. RLR RGD QTL W (SEQ ID NO:04, residues 528–537)
22. RVK RGD NFL W (SEQ ID NO:06, residues 504–513)

Preferred peptides derived from domain VI of netrin 2 and netrin 1:

23. DPC YDE (SEQ ID NO:04/06, residues 40–45/27–30)
24. RCI PE/DF VNA/S AFG KEV (SEQ ID NO:04/06, residues 51–65/38–52)
25. SST CGK PP (SEQ ID NO:04/06, residues 68–75/55–62)
26. A/SSD PKR/K AHP PA/S (SEQ ID NO:04, residues 97–107)
27. LTD LNN PH (SEQ ID NO:04, residues 109–116)
28. LTD LNT AA (SEQ ID NO:06, residues 80–87)
29. NL/MT CWR/Q S—(SEQ ID NO:04/06, residues 117–123/88–94)

The claimed netrins are isolated, partially pure or pure and are typically recombinantly produced. An "isolated" protein for example, is unaccompanied by at least some of the material with which it is associated in its natural state and constitutes at least about 0.5%, preferably at least about 2%, and more preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Aufubel, et al., Greene Publ. Assoc., Wiley-Interscience, N.Y.) or that are otherwise known in the art. The disclosed netrin peptides are also used as immunogens to generate specific polyclonal or monoclonal antibodies. See, Harlow and Lane (1988) Antibodies, A Laboratory Manual, Cold Spring Harbor Laboratory, for general methods.

The disclosed netrin compositions may be used to modulate axon outgrowth or guidance in situ or in vivo. For in vivo applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Netrins may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, imbedding or derivatizing fibers, such as collagen fibers, protein polymers, etc. with therapeutic proteins. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 μg/kg of the recipient and the concentration will generally be in the range of about 50 to 500 μg/ml in the dose administered. Other additives may be included, such as stabilizers, bactericides, etc. will be present in conventional amounts.

The invention provides netrin-specific binding agents including isolated binding targets such as membrane-bound netrin receptors and netrin-specific antibodies and binding agents identified in screens of natural and synthetic chemical libraries, and methods of identifying and making such agents, and their use in diagnosis, therapy and pharmaceutical development. Generally, netrin-specificity of the binding agent is shown by binding equilibrium constants. Such agents are capable of selectively binding a netrin, i.e. with an equilibrium constant at least about $10^7$ M$^{-1}$, preferably at least about $10^8$ M$^{-1}$, more preferably at least about $10^9$ M$^{-1}$. A wide variety of cell-based and cell-free assays may be used to demonstrate netrin-specific binding; preferred are rapid in vitro, cell-free assays such as mediating or inhibiting netrin-cell/protein binding, immunoassays, etc.

The invention also provides nucleic acids encoding the subject proteins, which nucleic acids may be part of netrin-expression vectors and may be incorporated into recombinant cells for expression and screening, transgenic animals for functional studies (e.g. the efficacy of candidate drugs for neural disease or injury), etc. and nucleic acid hybridization probes and replication/amplification primers having a netrin cDNA specific sequence. The hybridization probes contain a sequence common or complementary to the corresponding netrin gene sufficient to make the probe capable of specifically hybridizing to the corresponding netrin gene in the presence of laminin genes. Hybridization probes having in excess of 100 continuous bases of netrin gene sequence are generally capable of hybridizing to the corresponding netrin cDNA and remaining bound at a reduced final wash stringency of 0.2× SSC (0.9 M saline/0.09 M sodium citrate) and 0.1% SDS buffer at a temperature of 65° C.

Netrin genes, the term including natural genomic and mRNA/cDNA sequences, are characterized by sequence similarity to the disclosed netrin 1 and 2 cDNAs. Using the nucleic acid sequence search program BLASTX (Altschul et al. (1990) Basic Local Alignment Search Tool, J Mol Biol 215, 403–410), complete coding region (full length) netrin cDNA sequences provide a Probability P(N) score of less than $1.0e^{-200}$. In contrast, complete coding region nucleic acid sequence comparison of a netrin cDNA with the evolutionarily related laminin cDNAs provides P(N) scores exceeding $1.0e^{-144}$. In addition, netrin cDNAs generally show at least about 25% overall coding region pair-wise sequence identity with the disclosed netrins 1 and 2 cDNAs and at least about 35% domain V coding region pair-wise sequence identity. Furthermore, netrin genes are generally characterized by netrin gene-specific nucleic acid sequences invariant across the disclosed netrin 1 and 2 cDNAs as seen in their Nucleic Acid Alignments. Vertebrate netrin genes derive from vertebrates.

The subject nucleic acids are isolated, meaning they comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction. The subject nucleic acids find a wide variety of applications including use as translatable transcripts, hybridization probes, PCR primers, therapeutic nucleic acids, etc.; use in detecting the presence of netrin genes and gene transcripts, in detecting or amplifying nucleic acids encoding other netrins, and in gene therapy applications, e.g. antisense oligonucleotides capable of inhibiting the intracellular expression of a targeted netrin transcript.

The invention provides efficient methods of identifying pharmacological agents or lead compounds for agents capable of mimicking or modulating netrin function (e.g. bioactive netrin deletion mutants and netrin peptides). A wide variety of screens may be used; for example, cell-based assays for may be used for monitoring netrin function and in vitro binding assays may be used to identify netrin-specific binding agents. Tessier-Lavigne et al. (1988, supra) describe an assay for netrin activity and Kennedy et al. (1994) Cell 78, 425–435 describe a particularly convenient COS cell-based netrin expression assay. Preferred methods are amenable to automated, cost-effective high throughput screening of natural and synthetic chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

NETRIN GENE CLONING STRATEGIES

Vertebrate netrin genes are cloned using the using the two general cloning strategies illustrated below for mouse and human netrins. First, using a strategy based on the initial amplification of a PCR product, oligonucleotide primers are designed using amino acid and nucleic acid sequences conserved among the previously identified vertebrate netrin sequences. Using these primers, a partial cDNA clone, corresponding to the novel netrin of interest is amplified from cDNA ergonomic DNA from the tissue and organism of interest by PCR. This partial clone is then used to generate a labeled probe which is used to screen a cDNA library or genomic library at high stringency to isolate a full length cDNA corresponding to the clone of interest. We describe below how such a strategy, based on PCR followed by library screening, has been used to successfully isolate mouse netrin-1, Drosophila netrin-a, and two human netrin cDNAs. The second general strategy utilizes reduced stringency library screening (Sambrook et al., 1989). We demonstrate below the applicability of this method in the isolation of mouse netrin-2. In this case we amplified and incorporated $^{32}P$ into a probe which corresponded to domains VI and V in chicken netrin-2. Domains VI and V contain a number of regions of sequence which are well conserved among all vertebrate netrin family members isolated to this date. This probe was then used to screen an embryonic mouse brain cDNA library at reduced stringency. Our cloning of mouse netrin-2 using this method demonstrates that hybridization conditions are conveniently established which will detect netrin sequences between vertebrate species while avoiding significant background hybridization to non-netrin clones.

Our data identify netrin sequences common to the vertebrate netrins, mouse netrin-1, chicken netrin-1, and chicken netrin-2, which are not shared by the invertebrate netrin unc-6 as seen in netrin sequence alignments. The presence of these sequences, specific to vertebrates and conserved in all vertebrate netrins isolated, provides the necessary and sufficient sequence informative for generating primers and/or probes for any vertebrate netrin gene. In addition, amino acid sequence alignments similarly demonstrate that the vertebrate netrins define a structural class sharing common sequences not shared with the invertebrate species illustrated by C. elegans unc-6 and the *Drosophila Melanogaster* netrin-a. Furthermore the alignment between the Drosophila and the C, elegans sequences indicates there is a greater diversity of netrin amino acid sequence represented within the invertebrate phylum than is present within the sequences derived from the vertebrate phylum.

The following examples are offered by way of illustration and not by way of limitation.

EXAMPLES

We isolated chicken netrin 1 and 2 cDNAs as described in Sarafini et al. (1974) Cell 78:409–424. Based on the ckick netrin 1 and 2 cDNA sequences, we designed degenerate oligonucleotide primers and used these primers to amplify a cDNA encoding mouse netrin 1 from a murine cDNA library.

We isolated a mouse netrin-2 cDNA from a screen of a P0 (day of birth) mouse brain cDNA library (stratagene 937319: mouse P0 brain cDNA library in ZAPXP, oriented cloning). The probe used corresponded to sequences within domains VI and V of chicken netrin-2. Domain VI and V of the netrins contain regions of nucleic acid and amino acid sequence highly conserved in all netrins in each of the vertebrate species characterized to this date. The probe was labeled by incorporation of $^{32}P$ during PCR using a template of chicken netrin-2 cDNA.

$1 \times 10^6$ clones were screened at a reduced final wash stringency of 0.2× SSC and 0.1% SDS at 65 A1C (Sambrook et al., 1989). A single ~7.5 kb clone corresponding to mouse netrin-2 CDNA was obtained. Sequencing of this CDNA indicated that it comprises over 40% of the netrin coding sequence but is lacking sequence corresponding to the 5' coding sequence of mouse netrin-2. To isolate the 5' coding sequence from cDNA isolated from CDNA libraries, we have employed a combination of library screening and PCR using standard methods (Sambrook et al., 1989).

We first isolated a human netrin cDNA using the degenerate oligonucleotide primers. The primers were constructed using amino acid sequences conserved in the previously isolated chick and mouse netrin sequences as a guide. The starting material for PCR was 100 ng of human genomic DNA. PCR products were subcloned and individual clones containing inserts corresponding to human netrin sequence isolated using a Grunstein and Hogness screen (Sambrook, 1989). $^{32}$P was incorporated into a probe using PCR with a portion of the mouse netrin-1 cDNA clone as a template. The final wash of the filters was at a reduced stringency of 1× SSC and 0.1% SDS at 65° C. (Sambrook et al., 1989). This screen isolated an approximately 140 base pair human netrin cDNA clone. This cDNA fragment was used to isolate a longer human netrin cDNA from a Human fetal brain cDNA library (Stratagene cat#936206). The ~140 base pair human netrin cDNA was used as a template and 32P incorporated into a human netrin cDNA probe using PCR. 1×10$^6$ clones were screened at high stringency (Sambrook et al., 1989) identifying a single approximately 7 kb netrin cDNA. Sequence obtaining from the ends of this clone encode untranslated DNA sequence(see tables 9 and 10), indicating a full length clone. Internal sequence of the cDNA obtained using oligonucleotide primers corresponding to sequences contained in the ~140 clone, confirm and extend that sequence in the larger clone. Searches of the NBRF amino acid and nucleic acid sequence databases indicate that the published sequences with which this human cDNA shares the highest sequence identity are those of chicken netrin-1 and chicken netrin-2, the only vertebrate netrin sequences contained in the database at this date. In addition, these sequences encode amino acid sequences indicating that this clone represents a human netrin cDNA.

A partial cDNA was first amplified by PCR using non-degenerate primers designed using the codon usage for Drosophila as a guide. The particular sequences used were chosen on the basis of their conservation in the amino acid sequences of the invertebrate netrin gene unc-6 and the chicken netrin-1 and netrin-2 cDNAs. Nested PCR amplification was performed using 1 ng of total embryonic Drosophila cDNA as a template. A full length cDNA corresponding to *Drosophila melanogaster* netrin-a was then isolated by screening a cDNA library at high stringency using standard methods ( Sambrook et al., 1989).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying an agent which specifically binds a netrin, said method comprising the steps of:
contacting a prospective agent with a netrin comprising the amino acid sequence of SEQ ID NO: 4. 6, 8, 10 or 11, or portion thereof 25 residues in length, which portion modulates axon outgrowth or guidance or elicits a netrin-specific antibody; and,
determining if said agent specifically binds said netrin.

2. The method of claim 1, wherein the netrin comprises the amino acid sequence of SEQ ID NO: 4 or portion thereof 25 residues in length, which portion modulates axon outgrowth or guidance or elicits a netrin-specific antibody.

3. The method of claim 1, wherein the netrin comprises the amino acid sequence of SEQ ID NO: 6 or portion thereof 25 residues in length, which portion modulates axon outgrowth or guidance or elicits a netrin-specific antibody.

4. The method of claim 1, wherein the netrin comprises the amino acid sequence of SEQ ID NO: 8 or portion thereof 25 residues in length, which portion modulates axon outgrowth or guidance or elicits a netrin-specific antibody.

5. The method of claim 1, wherein the netrin comprises the amino acid sequence of SEQ ID NO: 10 or portion thereof 25 residues in length, which portion modulates axon outgrowth or guidance or elicits a netrin-specific antibody.

6. The method of claim 1, wherein the netrin comprises the amino acid sequence of SEQ ID NO: 11 or portion thereof 25 residues in length, which portion modulates axon outgrowth or guidance or elicits a netrin-specific antibody.

7. The method of claim 1, wherein the netrin comprises the amino acid sequence of SEQ ID NO: 4, 6, 8, 10 or 11.

8. The method of claim 1, wherein the netrin comprises an amino acid sequence selected from the group consisting of: SEQ ID NO:04, residues 289–294; SEQ ID NO:06, residues 265–270; SEQ ID NO:04, residues 296–304; SEQ ID NO:06, residues 272–280; SEQ ID NO:04, residues 308–315; SEQ ID NO:06, residues 284–291; SEQ ID NO:04, residues 320–338; SEQ ID NO:06, residues 296–319; SEQ ID NO:04, residues 345–350; SEQ ID NO:04, residues 352–368; SEQ ID NO:06, residues 328–344; SEQ ID NO:04, residues 373–380; SEQ ID NO:06, residues 349–356; SEQ ID NO:04, residues 385–401; SEQ ID NO:06, residues 361–377; SEQ ID NO:04, residues 408–416; SEQ ID NO:06, residues 384–392; SEQ ID NO:04, residues 418–423; SEQ ID NO:06, residues 394–399; SEQ ID NO:04, residues 427–434; SEQ ID NO:06, residues 403–410; SEQ ID NO:04, residues 439–451; SEQ ID NO:06, residues 415–427; SEQ ID NO:04, residues 454–460; SEQ ID NO:06, residues 429–435; SEQ ID NO:08, residues 451–456; SEQ ID NO:04, residues 466–478; SEQ ID NO:06, residues 442–454; SEQ ID NO:04, residues 485–499; SEQ ID NO:06, residues 461–475; SEQ ID NO:04, residues 513–523; SEQ ID NO:06, residues 489–499; SEQ ID NO:04, residues 545–550; SEQ ID NO:06, residues 521–526; SEQ ID NO:04, residues 573–584; SEQ ID NO:06, residues 549–560; SEQ ID NO:04, residues 528–537; SEQ ID NO:06, residues 504–513; SEQ ID NO:04, residues 40–45; SEQ ID NO:06, residues 27–30; SEQ ID NO:04, residues 51–65; SEQ ID NO:06, residues 38–52; SEQ ID NO:04, residues 68–75; SEQ ID NO:06, residues 55–62; SEQ ID NO:04, residues 97–107; SEQ ID NO:04, residues 109–116; SEQ ID NO:06, residues 80–87; SEQ ID NO:04, residues 117–123; and SEQ ID NO:06, residues 88–94.

9. The method of claim 1, wherein the netrin comprises an amino acid sequence selected from the group consisting of: SEQ ID NO:04, residues 289–294; SEQ ID NO:04, residues 296–304; SEQ ID NO:04, residues 308–315; SEQ ID NO:04, residues 320–338; SEQ ID NO:04, residues 345–350; SEQ ID NO:04, residues 352–368; SEQ ID NO:04, residues 373–380; SEQ ID NO:04, residues 385–401; SEQ ID NO:04, residues 408–416; SEQ ID NO:04, residues 418–423; SEQ ID NO:04, residues 427–434; SEQ ID NO:04, residues 439–451; SEQ ID NO:04, residues 454–460; SEQ ID NO:04, residues 466–478; SEQ ID NO:04, residues 485–499; SEQ ID NO:04, residues 513–523; SEQ ID NO:04, residues 545–550; SEQ ID NO:04, residues 573–584; SEQ ID NO:04, residues 528–537; SEQ ID NO:04, residues 40–45; SEQ ID NO:04, residues 51–65; SEQ ID NO:04, residues 68–75; SEQ ID NO:04, residues 97–107; SEQ ID NO:04, residues 109–116 and SEQ ID NO:04, residues 117–123.

10. The method of claim 1, wherein the netrin comprises an amino acid sequence selected from the group consisting of: SEQ ID NO:06, residues 265–270; SEQ ID NO:06, residues 272–280; SEQ ID NO:06, residues 284–291; SEQ ID NO:06, residues 296–319; SEQ ID NO:06, residues 328–344; SEQ ID NO:06, residues 349–356; SEQ ID NO:06, residues 361–377, SEQ ID NO:06, residues 384–392; SEQ ID NO:06, residues 394–399; SEQ ID NO:06, residues 403–410; SEQ ID NO:06, residues 415–427; SEQ ID NO:06, residues 429–435; SEQ ID NO:06, residues 442–454; SEQ ID NO:06, residues 461–475; SEQ ID NO:06, residues 489–499; SEQ ID NO:06, residues 521–526; SEQ ID NO:06, residues 549–560; SEQ ID NO:06, residues 504–513; SEQ ID NO:06, residues 27–30; SEQ ID NO:06, residues 38–52; SEQ ID NO:06, residues 55–62; SEQ ID NO:06, residues 80–87 and SEQ ID NO:06, residues 88–94.

11. The method of claim 1, wherein the netrin comprises an amino acid sequence selected from the group consisting of: SEQ ID NO:04, residues 289–294; SEQ ID NO:06, residues 265–270; SEQ ID NO:04, residues 296–304; SEQ ID NO:06, residues 272–280; SEQ ID NO:04, residues 308–315; SEQ ID NO:06, residues 284–291; SEQ ID NO:04, residues 320–338; SEQ ID NO:06, residues 296–319; SEQ ID NO:04, residues 345–350; SEQ ID NO:04, residues 352–368; SEQ ID NO:06, residues 328–344; SEQ ID NO:04, residues 373–380; SEQ ID NO:06, residues 349–356; SEQ ID NO:04, residues 385–401; SEQ ID NO:06, residues 361–377; SEQ ID NO:04, residues 408–416; SEQ ID NO:06, residues 384–392; SEQ ID NO:04, residues 418–423; SEQ ID NO:06, residues 394–399; SEQ ID NO:04, residues 427–434; SEQ ID NO:06, residues 403–410;SEQ ID NO:04, residues 439–451 and SEQ ID NO:06, residues 415–427.

12. The method of claim 1, wherein the netrin comprises an amino acid sequence selected from the group consisting of: SEQ ID NO:04, residues 454–460; SEQ ID NO:06, residues 429–435; SEQ ID NO:08, residues 451–456; SEQ ID NO:04, residues 466–478; SEQ ID NO:06, residues 442–454; SEQ ID NO:04, residues 485–499; SEQ ID NO:06, residues 461–475; SEQ ID NO:04, residues 513–523; SEQ ID NO:06, residues 489–499; SEQ ID NO:04, residues 545–550; SEQ ID NO:06, residues 521–526; SEQ ID NO:04, residues 573–584; SEQ ID NO:06, residues 549–560; SEQ ID NO:04, residues 528–537 and SEQ ID NO:06, residues 504–513.

13. The method of claim 1, wherein the netrin comprises an amino acid sequence selected from the group consisting of: SEQ ID NO:04, residues 40–45; SEQ ID NO:06, residues 27–30; SEQ ID NO:04, residues 51–65; SEQ ID NO:06, residues 38–52; SEQ ID NO:04, residues 68–75; SEQ ID NO:06, residues 55–62; SEQ ID NO:04, residues 97–107; SEQ ID NO:04, residues 109–116; SEQ ID NO:06, residues 80–87; SEQ ID NO:04, residues 117–123 and SEQ ID NO:06, residues 88–94.

14. A method of identifying a modulator of a netrin function, said method comprising the steps of:
contacting a prospective modulator with a netrin comprising the amino acid sequence of SEQ ID NO: 4, 6, 8, 10 or 11, or portion thereof 25 residues in length, which portion modulates axon outgrowth or guidance or elicits a netrin-specific antibody; and
determining if said modulator specifically modulates a function of said netrin, wherein said function is netrin-mediated modulation of axon outgrowth or guidance.

15. The method of claim 14, wherein the netrin comprises the amino acid sequence of SEQ ID NO: 4 or portion thereof 25 residues in length, which portion modulates axon outgrowth or guidance or elicits a netrin-specific antibody.

16. The method of claim 14, wherein the netrin comprises the amino acid sequence of SEQ ID NO: 6 or portion thereof 25 residues in length, which portion modulates axon outgrowth or guidance or elicits a netrin-specific antibody.

17. The method of claim 14, wherein the netrin comprises the amino acid sequence of SEQ ID NO: 8 or portion thereof 25 residues in length, which portion modulates axon outgrowth or guidance or elicits a netrin-specific antibody.

18. The method of claim 14, wherein the netrin comprises the amino acid sequence of SEQ ID NO: 10 or portion thereof 25 residues in length, which portion modulates axon outgrowth or guidance or elicits a netrin-specific antibody.

19. The method of claim 14, wherein the netrin comprises the amino acid sequence of SEQ ID NO: 11 or portion thereof 25 residues in length, which portion modulates axon outgrowth or guidance or elicits a netrin-specific antibody.

20. The method of claim 14, wherein the netrin comprises the amino acid sequence of SEQ ID NO: 4, 6, 8, 10 or 11.

21. The method of claim 14, wherein the netrin comprises an amino acid sequence selected from the group consisting of: SEQ ID NO:04, residues 289–294; SEQ ID NO:06, residues 265–270; SEQ ID NO:04, residues 296–304; SEQ ID NO:06, residues 272–280; SEQ ID NO:04, residues 308–315; SEQ ID NO:06, residues 284–291; SEQ ID NO:04, residues 320–338; SEQ ID NO:06, residues 296–319; SEQ ID NO:04, residues 345–350; SEQ ID NO:04, residues 352–368; SEQ ID NO:06, residues 328–344; SEQ ID NO:04, residues 373–380; SEQ ID NO:06, residues 349–356; SEQ ID NO:04, residues 385–401; SEQ ID NO:06, residues 361–377; SEQ ID NO:04, residues 408–416; SEQ ID NO:06, residues 384–392; SEQ ID NO:04, residues 418–423; SEQ ID NO:06, residues 394–399; SEQ ID NO:04, residues 427–434; SEQ ID NO:06, residues 403–410; SEQ ID NO:04, residues 439–451; SEQ ID NO:06, residues 415–427; SEQ ID NO:04, residues 454–460; SEQ ID NO:06, residues 429–435; SEQ ID NO:08, residues 451–456; SEQ ID NO:04, residues 466–478; SEQ ID NO:06, residues 442–454; SEQ ID NO:04, residues 485–499; SEQ ID NO:06, residues 461–475; SEQ ID NO:04, residues 513–523 SEQ ID NO:06, residues 489–499; SEQ ID NO:04, residues 545–550; SEQ ID NO:06, residues 521–526; SEQ ID NO:04, residues 573–584; SEQ ID NO:06, residues 549–560; SEQ ID NO:04, residues 528–537; SEQ ID NO:06, residues 504–513; SEQ ID NO:04, residues 40–45; SEQ ID NO:06, residues 27–30; SEQ ID NO:04, residues 51–65; SEQ ID NO:06, residues 38–52; SEQ ID NO:04, residues 68–75; SEQ ID NO:06, residues 55–62; SEQ ID NO:04, residues 97–107; SEQ ID NO:04, residues 109–116; SEQ ID NO:06, residues 80–87; SEQ ID NO:04, residues 117–123 and SEQ ID NO:06, residues 88–94.

22. The method of claim 14, wherein the netrin comprises an amino acid sequence selected from the group consisting of: SEQ ID NO:04, residues 289–294; SEQ ID NO:04, residues 296–304; SEQ ID NO:04, residues 308–315; SEQ ID NO:04, residues 320–338; SEQ ID NO:04, residues 345–350; SEQ ID NO:04, residues 352–368; SEQ ID NO:04, residues 373–380; SEQ ID NO:04, residues 385–401; SEQ ID NO:04, residues 408–416; SEQ ID NO:04, residues 418–423; SEQ ID NO:04, residues 427–434; SEQ ID NO:04, residues 439–451; SEQ ID NO:04, residues 454–460; SEQ ID NO:04, residues 466–478; SEQ ID NO:04, residues 485–499; SEQ ID NO:04, residues 513–523; SEQ ID NO:04, residues 545–550; SEQ ID NO:04, residues 573–584; SEQ ID NO:04, residues 528–537, SEQ ID NO:04, residues 40–45; SEQ ID NO:04, residues 51–65; SEQ ID NO:04, residues 68–75; SEQ ID NO:04, residues 97–107; SEQ ID NO:04, residues 109–116 and SEQ ID NO:04, residues 117–123.

23. The method of claim 14, wherein the netrin comprises an amino acid sequence selected from the group consisting of: SEQ ID NO:06, residues 265–270; SEQ ID NO:06, residues 272–280; SEQ ID NO:06, residues 284–291; SEQ ID NO:06, residues 296–319; SEQ ID NO:06, residues 328–344; SEQ ID NO:06, residues 349–356; SEQ ID NO:06, residues 361–377; SEQ ID NO:06, residues 384–392; SEQ ID NO:06, residues 394–399; SEQ ID NO:06, residues 403–410; SEQ ID NO:06, residues 415–427; SEQ ID NO:06, residues 429–435; SEQ ID NO:06, residues 442–454; SEQ ID NO:06, residues 461–475; SEQ ID NO:06, residues 489–499; SEQ ID NO:06, residues 521–526; SEQ ID NO:06, residues 549–560; SEQ ID NO:06, residues 504–513; SEQ ID NO:06, residues 27–30; SEQ ID NO:06, residues 38–52; SEQ ID NO:06, residues 55–62; SEQ ID NO:06, residues 80–87 and SEQ ID NO:06, residues 88–94.

24. The method of claim 14 wherein the netrin comprises an amino acid sequence selected from the group consisting of: SEQ ID NO:04, residues 289–294; SEQ ID NO:06, residues 265–270; SEQ ID NO:04, residues 296–304; SEQ ID NO:06, residues 272–280; SEQ ID NO:04, residues 308–315; SEQ ID NO:06, residues 284–291; SEQ ID NO:04, residues 320–338; SEQ ID NO:06, residues 296–319, SEQ ID NO:04, residues 345–350; SEQ ID NO:04, residues 352–368; SEQ ID NO:06, residues 328–344; SEQ ID NO:04, residues 373–380; SEQ ID NO:06, residues 349–356; SEQ ID NO:04, residues 385–401; SEQ ID NO:06, residues 361–377; SEQ ID NO:04, residues 408–416; SEQ ID NO:06, residues 384–392; SEQ ID NO:04, residues 418–423; SEQ ID NO:06, residues 394–399; SEQ ID NO:04, residues 427–434; SEQ ID NO:06, residues 403–410; SEQ ID NO:04, residues 439–451; and SEQ ID NO:06, residues 415–427.

25. The method of claim 14, wherein the netrin comprises an amino acid sequence selected from the group consisting of: SEQ ID NO:04, residues 454–460; SEQ ID NO:06, residues 429–435; SEQ ID NO:08, residues 451–456; SEQ ID NO:04, residues 466–478; SEQ ID NO:06, residues 442–454; SEQ ID NO:04, residues 485–499; SEQ ID NO:06, residues 461–475; SEQ ID NO:04, residues 513–523; SEQ ID NO:06, residues 489–499; SEQ ID NO:04, residues 545–550; SEQ ID NO:06, residues 521–526; SEQ ID NO:04, residues 573–584; SEQ ID NO:06, residues 549–560; SEQ ID NO:04, residues 528–537; and SEQ ID NO:06, residues 504–513.

26. The method of claim 14, wherein the netrin comprises an amino acid sequence selected from the group consisting of: SEQ ID NO:04, residues 40–45; SEQ ID NO:06, residues 27–30; SEQ ID NO:04, residues 51–65; SEQ ID NO:06, residues 38–52; SEQ ID NO:04, residues 68–75; SEQ ID NO:06, residues 55–62; SEQ ID NO:04, residues 97–107; SEQ ID NO:04, residues 109–116; SEQ ID NO:06, residues 80–87; SEQ ID NO:04, residues 117–123 and SEQ ID NO:06, residues 88–94.

\* \* \* \* \*